(12) United States Patent
Lv et al.

(10) Patent No.: US 12,144,732 B2
(45) Date of Patent: Nov. 19, 2024

(54) HEART VALVE PROSTHESIS ANCHORED TO INTERVENTRICULAR SEPTUM AND CONVEYING AND RELEASING METHOD THEREOF

(71) Applicant: JENSCARE SCIENTIFIC CO., LTD., Zhejiang (CN)

(72) Inventors: Shiwen Lv, Zhejiang (CN); Yibin Li, Zhejiang (CN); Zhi Chen, Zhejiang (CN)

(73) Assignee: JENSCARE SCIENTIFIC CO., LTD., Ningbo (CN)

( * ) Notice: Subject to any disclaimer, the term of this patent is extended or adjusted under 35 U.S.C. 154(b) by 7 days.

(21) Appl. No.: 17/824,625

(22) Filed: May 25, 2022

(65) Prior Publication Data

US 2022/0280288 A1 Sep. 8, 2022

Related U.S. Application Data

(62) Division of application No. 16/343,937, filed as application No. PCT/CN2017/107381 on Oct. 23, 2017, now Pat. No. 11,547,558.

(30) Foreign Application Priority Data

Oct. 24, 2016 (CN) .......................... 201610921114.9

(51) Int. Cl.
*A61F 2/24* (2006.01)
*A61B 17/04* (2006.01)
*A61B 17/06* (2006.01)

(52) U.S. Cl.
CPC .... *A61F 2/2418* (2013.01); *A61F 2210/0014* (2013.01); *A61F 2220/0008* (2013.01); *A61F 2220/0075* (2013.01)

(58) Field of Classification Search
None
See application file for complete search history.

(56) References Cited

U.S. PATENT DOCUMENTS

| 6,312,464 B1 | 11/2001 | Navia |
| 6,332,893 B1 | 12/2001 | Mortier et al. |
| (Continued) | | |

FOREIGN PATENT DOCUMENTS

| CN | 102438546 A | 5/2012 |
| CN | 102639179 B | 8/2012 |
| (Continued) | | |

OTHER PUBLICATIONS

International Search Report for PCT/CN2017/107381, Jan. 29, 2018.

(Continued)

*Primary Examiner* — Ann Schillinger
(74) *Attorney, Agent, or Firm* — Syncoda LLC; Feng Ma

(57) ABSTRACT

A heart valve prosthesis anchored to an interventricular septum. The heart valve prosthesis includes a valve supporting frame and a fixing device. The valve supporting frame includes a valve stitching section and an artificial valve, and the artificial valve is fixedly connected to the valve stitching section; the fixing device includes a fixing and supporting section and a fixing member, one end of the fixing and supporting section is connected to a proximal end of the valve stitching section, and another end of the fixing and supporting section is connected to the interventricular septum of a patient by the fixing member, to support the heart valve prosthesis and prevent the heart valve prosthesis from axially moving.

10 Claims, 10 Drawing Sheets

(56) References Cited

U.S. PATENT DOCUMENTS

| | | | |
|---|---|---|---|
| 6,358,277 B1 | 3/2002 | Duran | |
| 6,616,675 B1* | 9/2003 | Evard | A61B 18/1445 606/155 |
| 7,201,772 B2* | 4/2007 | Schwammenthal | A61F 2/2418 623/2.18 |
| 7,381,220 B2* | 6/2008 | Macoviak | A61F 2/2454 623/2.12 |
| 7,527,646 B2* | 5/2009 | Rahdert | A61F 2/2454 623/2.36 |
| 7,947,075 B2* | 5/2011 | Goetz | A61F 2/2418 623/2.18 |
| 8,449,599 B2 | 5/2013 | Chau et al. | |
| 8,579,964 B2 | 11/2013 | Lane et al. | |
| 8,926,691 B2* | 1/2015 | Chau | A61F 2/2409 606/108 |
| 8,992,604 B2* | 3/2015 | Gross | A61F 2/2412 623/2.11 |
| 9,017,399 B2* | 4/2015 | Gross | A61F 2/2418 623/2.11 |
| 9,034,032 B2* | 5/2015 | McLean | A61F 2/2436 623/2.12 |
| 9,072,603 B2* | 7/2015 | Tuval | A61F 2/2418 |
| 9,125,738 B2* | 9/2015 | Figulla | A61F 2/2418 |
| 9,125,740 B2* | 9/2015 | Morriss | A61F 2/2445 |
| 9,393,111 B2* | 7/2016 | Ma | A61F 2/2418 |
| 9,414,918 B2* | 8/2016 | Chau | A61F 2/2436 |
| 9,427,316 B2* | 8/2016 | Schweich, Jr. | A61F 2/2466 |
| 9,468,525 B2* | 10/2016 | Kovalsky | A61F 2/2418 |
| 9,517,131 B2* | 12/2016 | Nguyen | A61F 2/2454 |
| 9,662,202 B2* | 5/2017 | Quill | A61F 2/2418 |
| 9,730,791 B2* | 8/2017 | Ratz | A61F 2/2418 |
| 10,010,414 B2* | 7/2018 | Cooper | A61F 2/2418 |
| 10,117,744 B2* | 11/2018 | Ratz | A61F 2/2418 |
| 10,166,014 B2* | 1/2019 | Thambar | A61B 17/0057 |
| 10,226,335 B2* | 3/2019 | Cartledge | A61F 2/2418 |
| 10,426,605 B2* | 10/2019 | Ma | A61F 2/2418 |
| 10,449,049 B2* | 10/2019 | Li | A61F 2/246 |
| 10,492,908 B2* | 12/2019 | Hammer | A61F 2/2436 |
| 10,888,424 B2* | 1/2021 | Kuetting | A61F 2/2418 |
| 11,547,558 B2* | 1/2023 | Lv | A61F 2/2418 |
| 2004/0127982 A1 | 7/2004 | Machold et al. | |
| 2004/0138745 A1* | 7/2004 | Macoviak | A61F 2/2454 623/2.14 |
| 2004/0210307 A1* | 10/2004 | Khairkhahan | A61F 2/2418 623/2.34 |
| 2005/0038509 A1* | 2/2005 | Ashe | A61F 2/2448 623/2.38 |
| 2005/0075727 A1* | 4/2005 | Wheatley | A61F 2/2457 623/902 |
| 2006/0259135 A1* | 11/2006 | Navia | A61F 2/2457 623/2.11 |
| 2008/0243245 A1* | 10/2008 | Thambar | A61F 2/2436 623/2.11 |
| 2009/0005863 A1 | 1/2009 | Goetz et al. | |
| 2009/0276040 A1 | 11/2009 | Rowe et al. | |
| 2010/0036479 A1* | 2/2010 | Hill | A61F 2/2418 623/1.26 |
| 2010/0280606 A1* | 11/2010 | Naor | A61F 2/2418 623/2.18 |
| 2012/0101571 A1 | 4/2012 | Thambar et al. | |
| 2012/0179244 A1 | 7/2012 | Schankereli et al. | |
| 2013/0172978 A1 | 7/2013 | Vidlund et al. | |
| 2013/0172992 A1 | 7/2013 | Gross et al. | |
| 2013/0261737 A1* | 10/2013 | Costello | A61F 2/2418 623/2.11 |
| 2013/0261739 A1* | 10/2013 | Kuehn | A61F 2/2412 623/2.11 |
| 2014/0031928 A1* | 1/2014 | Murphy | A61F 2/2418 623/2.37 |
| 2015/0127097 A1 | 5/2015 | Neumann et al. | |
| 2015/0196390 A1 | 7/2015 | Ma et al. | |
| 2015/0351904 A1 | 12/2015 | Cooper et al. | |
| 2016/0038280 A1 | 2/2016 | Morriss et al. | |
| 2016/0074160 A1 | 3/2016 | Christianson et al. | |
| 2016/0095700 A1* | 4/2016 | Righini | A61F 2/2418 623/2.11 |
| 2016/0120643 A1* | 5/2016 | Kupumbati | A61F 2/2436 623/2.11 |
| 2017/0112618 A1 | 4/2017 | Li et al. | |
| 2017/0258589 A1 | 9/2017 | Pham et al. | |
| 2018/0014931 A1* | 1/2018 | Morriss | A61F 2/2418 |

FOREIGN PATENT DOCUMENTS

| | | |
|---|---|---|
| CN | 103068341 A | 4/2013 |
| CN | 104394802 A | 3/2015 |
| CN | 105101911 A | 11/2015 |
| CN | 105520792 A | 4/2016 |
| CN | 106618798 A | 5/2017 |
| WO | 2014021905 A1 | 2/2014 |
| WO | 2016154166 A1 | 9/2016 |

OTHER PUBLICATIONS

Supplementary European Search Report for EP 17863597 dated Feb. 26, 2020.
Examination Report for EU 17863597.5 dated Dec. 8, 2020.
Second Examination Report for EU 17863597.5 dated May 31, 2021.
English language abstract for CN 106618798 A (2017).
English language abstract for CN 103068341 A (2013).
English language abstract for CN 105520792 A (2016).
English language abstract for CN 105101911 A (2015).

* cited by examiner

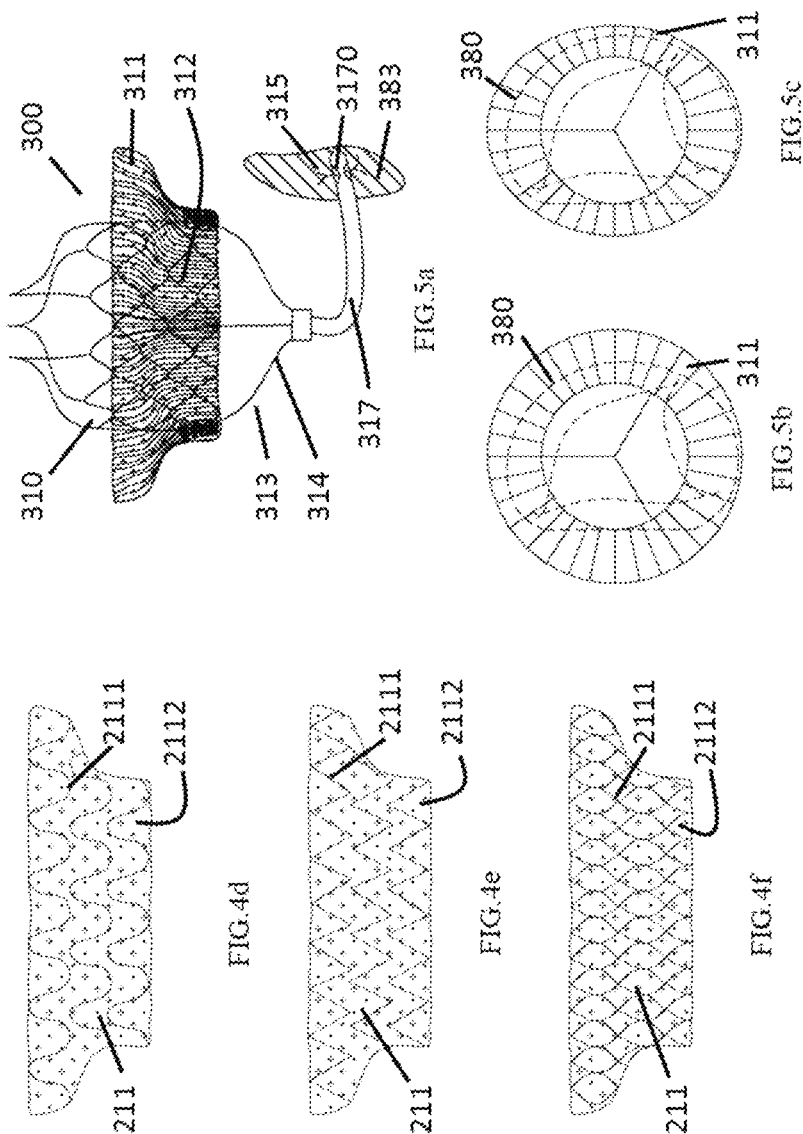

HEART VALVE PROSTHESIS ANCHORED TO INTERVENTRICULAR SEPTUM AND CONVEYING AND RELEASING METHOD THEREOF

CROSS-REFERENCE TO RELATED APPLICATIONS

This application is a divisional application of U.S. patent application Ser. No. 16/343,937, filed on Apr. 22, 2019, which is a National stage of International Application No. PCT/CN2017/107381, filed on Oct. 23, 2017. The International Application claims priority to Chinese Patent Application No. 201610921114.9, filed on Oct. 24, 2016. The afore-mentioned patent applications are hereby incorporated by reference in their entireties.

TECHNICAL FIELD

The present application relates to the field of medical equipment, and particularly relates to a heart valve prosthesis anchored to an interventricular septum and a conveying and releasing method thereof.

BACKGROUND

Mitral valve is located at the left atrioventricular orifice, and includes five parts: valve annulus, valve leaflet, chordae tendineae, papillary muscle and commissure, and the mitral valve's accurate name in anatomia is mitral apparatus or mitral complex. Mitral valve annulus is a fibrous tissue strip attached to the edge of the left atrioventricular orifice, and is in an irregular "D" shape. The front one third of the mitral valve annulus is a continuation of the anterior valve and the aorta, the angles formed between the atrium corresponding to the anterior leaflet and the mitral valve are different from the angles formed between the atrium corresponding to the posterior leaflet and the mitral valve annulus, and the atrium includes the left atrial appendage. Mitral valve dysfunction is one of the most common heart diseases, such as mitral insufficiency caused by mitral valve prolapse, mitral stenosis caused by valve lesion due to rheumatic inflammation.

Mitral insufficiency can be classified into three types: functional, degenerative and mixed mitral insufficiency. The most common ones are degenerative mitral insufficiency and functional mitral insufficiency. The functional mitral insufficiency is generally secondary to motor function impairment of left ventricular wall, left ventricle dilatation and papillary muscle dysfunction, and is common in patients of heart failure. Such patients also include the ones of ischemic mitral insufficiency secondary to coronary heart disease and mitral insufficiency related to non-ischemic cardiomyopathy. Degenerative mitral valve reflux diseases are generally considered as the pathological changes of the valve structure or the pathological changes of the subvalvular structure, including the abnormal extension or rupture of the chordae tendineae.

Mitral stenosis is the most common type of rheumatic valvular heart diseases, in which 40% of the patients have simple mitral stenosis. Because of the recurrent rheumatic fever, the mitral stenosis in the early stage is mainly caused by edema, inflammation and neoplasm (exudate) of the valve commissure and its basis points, and in the later healing process, because of the sediment of fibrous protein and fibrous changes, gradually formed are adhesion and fusion of the boundary between the anterior and posterior valve leaflets, valve thickening, valve coarsening, valve sclerosis, valve calcification, and chordae tendineae shortening and adhesion, which limit the mobility and opening of the valve, and cause valve orifice stenosis. Other rare etiologies include senile mitral valve annulus or sub-annulus calcification, congenital stenosis and connective tissue diseases and so on.

Tricuspid valve is located at the right atrioventricular orifice. A common disease of the tricuspid valve is tricuspid insufficiency, that is, in the contraction period, the blood flows back from the right ventricle into the right atrium, which causes the excessive dilatation of the right atrium, increased pressure, and backflow disorder of venous blood. Because of the increasing load, a compensation on the right ventricle occurs. As a result, the right ventricle becomes fat and thick, and right heart failure easily happens.

Tricuspid regurgitation is generally caused by pulmonary arterial hypertension, right ventricular dilatation and tricuspid valve annulus dilatation. Clinically the expression of the etiologies (such as left heart failure and pulmonary arterial hypertension) of tricuspid regurgitation is common, and once tricuspid regurgitation arises, the symptoms of right heart failure such as fatigue, ascites, edema, hepatalgia, dyspepsia and anorexia are aggravated. Mild tricuspid regurgitation does not have obvious clinical symptoms, but operative treatment is required for serious tricuspid regurgitation.

The traditional treatments for the diseases of mitral valve and tricuspid valve include medication for mild to severe regurgitation, and surgical methods having the corresponding operation indications. Wherein, the surgical methods further comprise valve replacement and valve repairment. In the surgical methods, the typical thoracotomy and open heart surgeries have too large invasiveness, and an extracorporeal circulation needs to be established, therefore, there will be a high complication incidence and a risk of infection. Many patients cannot bear the huge surgical risk and have to helplessly wait for death.

Since the report of the first surgery of aortic valve intervention and replacement, many corporations have made a lot of efforts in the technique of aortic valve intervention, and the technique is becoming increasingly mature. However, as for the intervention treatment of atrioventricular valve, a relatively large blank still exists in the art. A few products for the intervention treatment for atrioventricular valve are applied in transcatheter intervention valve shaping and repairment, but in the aspect of transcatheter intervention valve replacement, no mature products are available in the world. What listed as follows are several kinds of technique for transcutaneous intervention valve replacement of mitral valve, which are mostly in the stage of animal experiments or clinical trials, and all have their individual limitations.

The Chinese patent publication No. CN102639179B and the U.S. Pat. No. 8,449,599 describe a prosthetic apparatus for mitral valve replacement of the Edwards Lifesciences Corporation. The prosthetic apparatus is configured to be implanted into the native mitral valve region of the heart; the native mitral valve has a native annulus and a native valve leaflets. The prosthetic apparatus includes a tube-shaped main body. The tube-shaped main body includes a lumen, an atrium end and a ventricle end, which are configured to allow the blood to flow through, and is configured to be placed within the native annulus. The main body may be radially compressed to be in a radially compressed state, so as to be delivered into the heart, and be self-expandable from the compressed state to a radially expanded state. The prosthetic apparatus further includes at least one fixing device connected with the main body and disposed outside the main body. The fixing device and the main body are connected, so that when the main body is in the expanded state, the at least one fixing device is configured to hook the periphery of the native leaflets, to limit a leaflet receiving space between at least one fixing device and the main body. The prosthetic apparatus further includes an annular flange portion extending radially outward from an atrial end of the main body, and the annular flange portion comprises an atrial sealing member that blocks blood from flowing beyond the atrial end of the main body disposed outside the main body when the prosthetic apparatus is implanted. Regarding the fixing mode employed by the technique, because the fixing device defined in the independent claim is disposed outside the main body, the native leaflets will be smoothly placed between the exterior side surface of the blood channel of the main body of the supporting frame and the inner side surface of the anchoring device, thus the fastness of the fixing completely relies on the friction between the fixing device and the main body. Furthermore, after being clamped, the native valve is always in the valve leaflet opening position and spreading state of the diastole period, and the large area annular blocks the blood flow in the left ventricular outflow tract, thus the blood that should flow from the left ventricle into the aorta during this period is partially blocked and flows back to the left ventricle. After long-term implantation, disorders such as heart failure will arise. Especially when the native valve leaflet of the patient has severe calcification, the valve clamping mechanism of the native valve leaflet increases the difficulty of the surgery operation. In the clinical application of this product of Edwards, the native valve leaflet of the patient were not able to be correctly grabbed, which causes multiple cases of surgery failure, instrument displacement and urgent transferring the patients to surgical thoracotomy operation native valve, and the patients finally died or were faced with the risk of death. Finally, the technique of clamping the native valve leaflet inevitably affects the function of the supporting frame of returning to the sheath, and once released, it cannot be withdrawn, which brings a large operation risk.

The Chinese patent No. CN201180020556 introduces a mitral valve prosthesis of Medtronic corporation, which comprises an inner supporting structure that has a downstream section and an upstream section, wherein a cross-sectional area of the upstream section is greater than that of the downstream section, and the inner supporting structure is configured to be at least partially positioned on the atrial side of the native valve complex, and to exert an axial force toward the left ventricle; and an outer supporting structure, having two or more engagement arms attached to the inner support structure. Wherein, the prosthesis, after being transplanted, is configured to clamp part of the leaflet of the protogenetic valve between the inner supporting structure and the engagement arms. As similar to the design of Edwards, the upstream section having a greater cross-sectional area abuts on the mitral valve annulus, and the engagement arms of the outer supporting structure grab the native mitral valve of the patient. The supporting frame as a whole is a cylindrical symmetrical structure, so doctors are still required to select a valve with a higher specification in surgery to provide a sufficient supporting force. The valve with huge diameter severely blocks the blood supply from the left ventricular outflow tract, and in the aortic valve orifice, the flow rate is increased and the pressure is boosted, which, for a long time, easily causes heart failure. Moreover, the valve with relatively large diameter entirely clings to the valve annulus directly, and will press the adjacent tissues including the aortic valve annulus.

The Chinese patent No. CN201610074782 provides a D-shaped intervention-type artificial heart valve, comprising a supporting frame, a valve leaflet provided on the inner side of the supporting frame, and a covering film provided on the supporting frame body wall. The supporting frame comprises a first sub-supporting frame, a second sub-supporting frame and a third sub-supporting frame that are sequentially connected. The first sub-supporting frame is a net-like tube; the second sub-supporting frame is a net-like tube whose cross-section is D-shaped; and the third sub-supporting frame is a net-like tube with a horn shape. The maximum tube diameter of the first sub-supporting frame is the same as the tube diameter of the second sub-supporting frame, and the minimum tube diameter of the third sub-supporting frame is the same as the tube diameter of the second sub-supporting frame. Although the patent states that the so-called D-shaped net-like tube may match with the shape of the receiving space that is enclosed by the protogenetic body wall of the in-situ mitral valve, and compared with a supporting frame whose cross-section is circular, the D-shaped net-like tube may avoid the narrowing of the outflow tract of the heart caused by the excessive stress exerted on the non-round contour of the mitral valve by the supporting frame, the problems of the technique are that, even if the cross-section of the supporting frame is modified to be D-shape, the direct contact of the whole lattice structure with the mitral valve annulus still exerts stress on its surrounding tissue; moreover, in the technical solution, the maximum tube diameter of the first sub-supporting frame is the same as the tube diameter of the second sub-supporting frame, which means that the diameter of the cross-section of the supporting frame is still at least equal to the diameter of the mitral valve annulus, therefore, the influence exerted on the outflow tract by the huge supporting frame itself still exists; and finally, in the technical solution, the second sub-supporting frame is configured to be D-shaped, and the valve leaflet is stitched to the supporting frame, and the non-round region definitely affects the clinging state after the valve leaflet is stitched. Although the technique does not particularly disclose the stitching mode of the valve, it can still be seen from the drawings that the valve leaflet is a three-leaf valve. Therefore, the non-round suture will be harmful to the closing property of the valve leaflet and long-term valve leaflet fatigue.

The U.S. patent publication No. US20160074160 discloses a valve supporting frame structure, comprising an expanded external supporting frame made of a shape memory alloy, and an internal supporting frame made of a shape memory alloy; wherein the internal supporting frame includes two portions, and in an initial state, the first portion is an expanded structure, and the second portion is a compressed structure; an artificial valve is provided at the first portion of the internal supporting frame, and the second portion is provided with a string; and the internal supporting frame and the external supporting frame are connected and fixed. The problems of the solution are that, the expanded external supporting frame still supports and radially expands the original valve annulus, and the relatively large cross-sectional area of the supporting frame definitely takes effects on the outflow tract. In addition, the portion of the external supporting frame that is disposed on the mitral valve annulus cannot conform to the non-uniform contour of the atrial wall or of the native valve annulus of the patient, pressing the aorta or other heart tissues, and moreover, the leak resistance effect is poor.

The current clinical results indicate that, there are no ideal products for valve intervention and replacement of atrioventricular valve. The major reason is that, both of the mitral valve and the tricuspid valve have particular physiological structures, and the physiological environments under the valve annulus are complicated, which makes it difficult to accurately position and fix the products. The problems of the prior art are summarized as follows: (1) the conventional anchoring techniques mostly rely on the supporting force exerted on the atrioventricular valve annulus by the supporting frame; and doctors usually select a valve specification larger than the valve annulus of the autogenous atrioventricular valve of the patient, so as to conform to the contour of the mitral valve tissue, thus the huge supporting frame itself not only affects the outflow tract, but also easily presses the surrounding tissues, and further blocks the blood flow in the left ventricular outflow tract; (2) in the prior art, the supporting frame portion disposed in the atrium mostly configured to be a lattice, the huge supporting force of which easily presses the heart tissue; and (3) as for the mitral valve replacement, the supporting frame specification is too large, and the anterior valve of the mitral valve is easily pushed toward the left ventricular outflow tract; and the design of clamping the valve leaflet, which is introduced to fix the anterior valve of the mitral valve, makes the releasing step extremely complicated and be influenced by the calcification degree of the valve leaflet, which affects the success rate of the operation.

In conclusion, although the above described techniques individually have certain effects on the atrioventricular valve replacement, they still have defects. In the field of surgical treatment for valve lesion, a novel heart valve prosthesis is urgently needed to solve the above problems.

SUMMARY OF THE DISCLOSURE

The objective of the present application is to overcome the defects in the prior art. For the patients that require intervention valve replacement due to mitral valve or tricuspid valve insufficiency or stenosis, the present application provides a heart valve prosthesis anchored to an interventricular septum, and a conveying and releasing method of the heart valve prosthesis. The present application solves the problems of the anchoring technology in the prior art, which are caused by radially dilating the native valve annulus of the patient, and on the basis of ensuring the anchoring effects of the implanted valve, may reduce the influences on the outflow tract after the supporting frame is released, and avoids the traction for the valve annulus of the native valve.

An objective of the present application is achieved by the following technical solution:
 a heart valve prosthesis anchored to an interventricular septum comprises a valve supporting frame and a fixing device; the valve supporting frame comprises a valve stitching section and an artificial valve; the artificial valve is fixedly connected to the valve stitching section; the fixing device comprises a fixing and supporting section and a fixing member; one end of the fixing and supporting section is connected to a proximal portion of the valve stitching section; and another end of the fixing and supporting section is connected to an interventricular septum of a patient by the fixing member to support the heart valve prosthesis and limit axial movement of the heart valve prosthesis.

The objectives of the present application may also be further realized by following technical solutions:
Preferably, the fixing and supporting section is provided with a curved section, which is configured to enable a proximal portion of the fixing and supporting section to cling to the interventricular septum of the patient. More preferably, the part of the fixing and supporting section that contacts the interventricular septum of the patient is a straight line section.

Preferably, the fixing and supporting section comprises a plurality of rods or wires; one end of each of the plurality of rods or wires is connected to the valve stitching section; and another end of each of the plurality of rods or wires is connected to the interventricular septum of the patient by the fixing member.

Preferably, the fixing and supporting section comprises a plurality of rods or wires; one end of each of the plurality of rods or wires is connected to the valve stitching section; and other ends of the plurality of rods or wires are mutually connected and are connected to the interventricular septum of the patient by the fixing member.

More preferably, on the circumferential circular arc where the outer edge of the valve stitching section is located, the largest arc length that is formed by the connection points between the plurality of rods or wires and the valve stitching section is greater than or equal to a quarter of the perimeter of the valve stitching section.

Preferably, the fixing and supporting section is formed by extending a skeleton of a proximal end of the valve stitching section.

Preferably, the fixing and supporting section is covered with a film.

Preferably, the fixing and supporting section is a triangular structure, or the fixing and supporting section is an arcuate structure, or the fixing and supporting section is a net-like structure. More preferably, the fixing and supporting section is provided therein with an enhancing rod.

Preferably, the fixing and supporting section and the fixing member are an integral structure, and the fixing member is barbs, or the fixing member is a sharp structure.

Preferably, the fixing device comprises a fixing member pushing system, and the fixing member pushing system pushes the fixing member so that one end of the fixing and supporting section is fixed on the interventricular septum of the patient.

Preferably, the fixing member is an anchoring needle, and the tail portion of the anchoring needle is provided with a stopper.

More preferably, the fixing member pushing system comprises a guide rail and a mandril; the guide rail is provided on the fixing and supporting section; the ends of the guide rail have a necking; the anchoring needle and the mandril are provided within the guide rail; by operating the mandril, the needle point portion of the anchoring needle passes through the guide rail and is inserted into the interventricular septum of the patient; and the diameter of the stopper is greater than the caliber of the necking.

More preferably, the stopper is provided with a connector, and the connector is a wire-shaped member; one end of the connector is connected to the fixing and supporting section, and the other end of the connector is connected to the stopper. Such a design mainly can ensure that the implanting instrument is detachably connected with the pushing system, thereby improving the accuracy of the needle inserting, and preventing the anchoring needle from deviating from the predetermined needle inserting point.

Preferably, the fixing and supporting section is an inverted cone-shaped structure; one end of the fixing and supporting section, which has a larger diameter, is connected to the proximal end of the valve stitching section; one end of the fixing and supporting section, which has a smaller diameter, is connected to a connecting rod; the connecting rod is rigid; a fixing member is arranged at the proximal portion of the connecting rod; and in a free state, the fixing member is fixed on the interventricular septum.

More preferably, the proximal portion of the connecting rod is a hollow tube; the tube wall is provided with an opening; and in a free state, the furthest distal end of the fixing member protrudes out of the opening on the hollow tube and inserts into the interventricular septum. The furthest distal end of the fixing member is sharp, and the distal portion of the fixing member is pre-shaped. The distal portion of the fixing member is pre-shaped to be one of or a combination of the following shapes: spiral, circle, arc, a combination of arc and straight line, branched double hooks, three-dimensional bent shape and multisection bent shape, and the distal end of the fixing member does not have a barb or has one or more barbs.

Preferably, the fixing member is a supporting frame having two larger end portions and a smaller middle portion, and is formed by a shape memory alloy.

Preferably, the heart valve prosthesis further comprises an auxiliary fixing device; one end of the auxiliary fixing device is connected to a distal end of the valve stitching section, and the other end of the auxiliary fixing device is fixed on an atrium tissue or fixed in a blood vessel of the patient.

More preferably, the auxiliary fixing device is a rod or a wire, or the auxiliary fixing device is a supporting frame.

Preferably, the heart valve prosthesis further comprises an auxiliary stabilizing device; a proximal end of the auxiliary stabilizing device is connected to the fixing and supporting section, or a proximal end of the auxiliary stabilizing device is connected to the fixing member, and a distal end of the auxiliary stabilizing device is connected to the valve stitching section.

More preferably, the auxiliary stabilizing device is a wire or a rod.

Preferably, in a longitudinal section parallel to a central axis of the artificial valve, the projections of the valve stitching section, of the fixing and supporting section and of the auxiliary stabilizing device are connected to become a closed structure.

Preferably, in a cross-section perpendicular to a central axis of the artificial valve, a cross-sectional area of the valve stitching section is less than a cross-sectional area of a native valve annulus of the patient, which prevents the valve stitching section radially dilating the native valve annulus of the patient.

Preferably, the heart valve prosthesis further comprises a ring; the ring is connected to the valve stitching section, and in a free state, the ring is disposed in an atrium of the patient.

Preferably, the ring clings to a native valve annulus of the patient.

Preferably, and in a free state, a cross-sectional area of the ring is greater than a cross-sectional area of a native valve annulus of the patient, and the ring is capable of conforming to a non-uniform contour of an atrial wall or of the native valve annulus of the patient and not restricting a contraction function of the atrium.

Preferably, in a cross-section perpendicular to a central axis of the artificial valve, the projection of the ring is a ring-shaped structure; the ring-shaped structure comprises a circular structure, an elliptic structure or a D-shaped structure; and the valve stitching section is disposed in the ring.

Preferably, in a cross-section perpendicular to a central axis of the artificial valve, a center of the valve stitching section and a center of the ring are not coincident.

More preferably, when the heart valve prosthesis is used for mitral valve intervention and replacement, the central axis of the valve stitching section deviates toward the posterior valve region of the mitral valve of the patient.

More preferably, when the heart valve prosthesis is used for tricuspid valve intervention and replacement, the central axis of the valve stitching section deviates toward the cuspis medialis region of the tricuspid valve of the patient.

Preferably, in a longitudinal section parallel to a central axis of the artificial valve, the projection of the ring is a disk-like structure or a bowl-like structure.

Preferably, the valve stitching section is a tube-like lattice structure, or the valve stitching section is a tube-like wave-shaped structure.

Preferably, a distal skeleton of the valve stitching section is provided with an extended section. Such a design enables the supporting frame to be controllably released. More preferably, the extension section and the valve stitching section are detachably connected. Such a design ensures that the extension section can be withdrawn from the human body while the supporting frame is ensured to be controllably released, thereby greatly reducing the implant, reducing the contact and stimulation to the atrium, and eliminating the limitation to the valve-in-valve implantation in future.

Preferably, the proximal skeleton of the valve stitching section is partially extended. Such a design enables the ring to expand firstly while the proximal end of the supporting frame remains compressed, which facilitates adjusting the position of the supporting frame, thereby preventing the proximal end of the supporting frame from stabbing the blood vessel wall due to expanding in the adjusting process.

Preferably, the ring has a skeleton made of a shape memory alloy; the skeleton is partially or entirely covered with a film, and the film material comprises metal material, polytetrafluoroethylene, polyethylene, polypropylene, terylene or animal-derived material.

More preferably, the skeleton includes a plurality of supporting rods; or the skeleton is a wave-shaped structure, a saw-shaped structure or a lattice structure that is formed by winding a metal memory material wire. The width of the supporting rods or the diameter of the metal memory material wire (for example, a nickel titanium alloy wire) is in the range of 0.1-0.6 mm.

Preferably, the ring is provided with a barb, and in a free state, the barb is inserted into an autologous tissue of the patient.

Preferably, the ring and the valve stitching section are made separately and independently and then are connected to form an integral structure.

Preferably, the ring and the valve stitching section are an integral structure, and the ring is formed by part of the rods in the skeleton of the valve stitching section.

Preferably, an outer surface of the valve stitching section is further provided with a filling device.

Preferably, the filling device has a skeleton made of a shape memory alloy; the skeleton is partially or entirely covered with a film; and the film material comprises metal material, polytetrafluoroethylene, polyethylene, polypropylene, terylene or animal-derived material.

Preferably, in a cross-section perpendicular to a central axis of the artificial valve, the projection of the filling device is a ring-shaped structure, and the ring-shaped structure comprises a circular ring structure or a D-shaped ring structure.

Preferably, the filling device and the ring are an integral structure.

Another objective of the present application is realized by the following technical solutions:

a method for conveying and releasing the heart valve prosthesis anchored to an interventricular septum comprises the following steps:
- a. introducing a conveying conduit loaded with the heart valve prosthesis to an atrioventricular valve annulus via a minimally invasive incision in the atrial wall;
- b. operating the conveying conduit, to release the fixing device;
- c. operating the conveying conduit, to release the valve stitching section;
- d. operating the conveying conduit, to make the fixing member be inserted into the interventricular septum of the patient; and
- e. withdrawing the conveying conduit from a human body.

Preferably, the method further comprises the following steps between the step c and the step d:
- c1. operating the conveying conduit, to partially release the valve stitching section and make the valve stitching section not be completely detached from the conveying conduit;
- c2. operating the conveying conduit, to release the ring, and positioning through the ring; and
- c3. operating the conveying conduit, to completely release the valve stitching section.

The advantages of the present application over the prior art are:

1. In the design of most of the products in the prior art, a supporting frame supports the valve annulus; what different from the prior art are that, in the present application, the fixing and supporting section is fixed on the interventricular septum of the patient by the fixing member, and such an anchoring mode enables the supporting frame to obtain a anchoring force large enough, without radially dilating the native valve annulus of the patient.

2. In the present application, the fixing and supporting section is provided with a curved section, thereby enabling the proximal end portion of the fixing and supporting section to cling to the interventricular septum of the patient, and the contact part of the distal end of the fixing and supporting section with the interventricular septum of the patient is a straight line section. Such a design can increase the contact area between the fixing and supporting section and the interventricular septum of the patient to the utmost extent, thereby enhancing the anchoring effect.

3. In the present application, on the circumferential circular arc where the outer edge of the valve stitching section is located, the largest arc length that is formed by the connection points between the plurality of rods and the valve stitching section is greater than or equal to a quarter of the perimeter of the valve stitching section. The advantage of such a design is that the fulcrum of the fixing and supporting section, which is disposed on the valve stitching section, can provide sufficient supporting strength and rigidity, thereby avoiding the incline of the valve stitching section.

4. In the present application, the auxiliary fixing device is provided. The auxiliary fixing device is fixed on the atrium tissue or fixed in the blood vessel of the patient, and prevents the displacement or disengagement of the implant by means of upper and lower location limiting, thereby enhancing the anchoring fastness of the implant.

5. In the present application, the auxiliary stabilizing device is provided. In a longitudinal section parallel to a central axis of the artificial valve, the projections of the valve stitching section, of the fixing and supporting section and of the auxiliary stabilizing device are connected to become a closed structure, which enables the implant to be more secure in the target position while ensuring the operation convenience of fixing on one side, thereby preventing the heart valve prosthesis from losing balance in the body of the patient.

6. As different from the concentric structure of most of the conventional products in the prior art, in the present application, in a cross-section perpendicular to a central axis of the artificial valve, a center of the valve stitching section and a center of the ring are not coincident. When the heart valve prosthesis is used for mitral valve intervention and replacement, the central axis of the valve stitching section deviates toward the posterior valve region of the mitral valve of the patient, which can further reduce the block to the left ventricular outflow tract. When the heart valve prosthesis is used for tricuspid valve intervention and replacement, the central axis of the valve stitching section deviates toward the cuspis medialis region of the tricuspid valve of the patient, which facilitates the fixing and supporting section clinging to the target anchoring region, thereby obtaining a more ideal anchoring effect, and more stable movement of the valve.

7. What different from the design of most of the products in the prior art, in which a supporting frame supports the valve annulus, are that, in the present application, in a cross-section perpendicular to a central axis of the artificial valve, the projection area of the valve stitching section is less than the projection area of the native valve annulus of the patient, which prevents the valve stitching section radially dilating the native valve annulus of the patient, thereby not only reducing the influence on the outflow tract after the supporting frame is released, and avoiding the traction to the protogenetic valve annulus, but also ensuring that the opening area of the valve will not change greatly because of the huge difference between the annulus of patients, and optimizing the performance of the valve. Moreover, the manufacturers may reduce the product specifications, which alleviate the goods stocking pressure of the manufacturers.

8. In the product in the prior art, the supporting frames located in the atrium mostly employs the lattice form, and the huge supporting force of the supporting frame easily presses the heart tissue, and the leak resistance effect is unsatisfying. What different from the supporting frame in the prior art are that, the ring of the present application is disposed in the atrium of the patient and clings to the native valve annulus of the patient, and the ring may conform to the non-uniform contour of the atrial wall or of the native valve annulus of the patient, thereby improving the leak resistance effect.

9. In the present application, a distal skeleton of the valve stitching section is provided with an extended section, and the extended section and the valve stitching section are detachably connected. Such a design ensures that the extended section may be withdrawn from the human body while the supporting frame is ensured to be controllably released, thereby greatly reducing the implant, reducing the contact and stimulation to the atrium, facilitating the conveying system being removed from the human body, and eliminating the limitation to the valve-in-valve implantation in future.

BRIEF DESCRIPTION OF DRAWINGS

FIGS. 4a-4f are schematic diagrams illustrating multiple embodiments of the present application.

FIGS. 5a-5d are schematic diagrams illustrating multiple embodiments of the present application.

FIGS. 9a-9f are schematic diagrams illustrating multiple embodiments of the present application, wherein FIG. 9b is a sectional view of FIG. 9a.

DETAILED DESCRIPTION

Figure 1A:
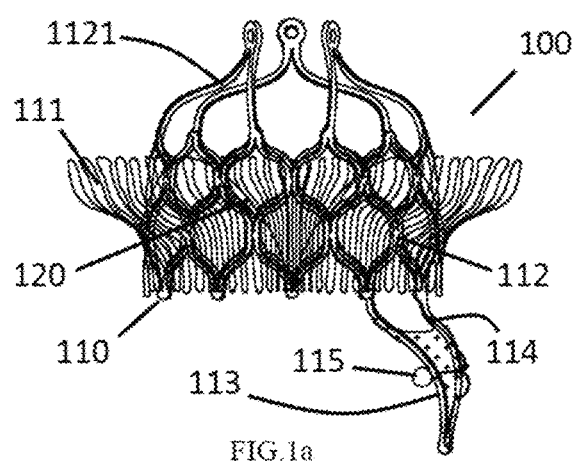
FIGS. 1a-1c are schematic diagrams illustrating an embodiment of the present application.

In order to make the objectives, the technical solutions and the advantages of the present application more apparent and better understood, the present application will be described in more details by referring to the accompanying figures and the embodiments.

In the present application, the distal end refers to the end far away from the cardiac apex, and the proximal end refers to the end near to the cardiac apex.

Embodiment 1

For a long time, large valve manufacturers, whether Edwards Corporation or Medtronic Corporation, all achieve a sufficient anchoring force of the supporting frame by increasing the radial expansion ratio of the supporting frame to the valve annulus, which has already been widely applied and become a common view in the field of aortic valve intervention and replacement, and in the field of pulmonary valve intervention and replacement (generally, 10%-15% is the ideal perimeter expansion ratio). Moreover, subsequently, both Jenavalve Corporation and Symetic Corporation applied the valve leaflet clamping mechanism to the products, which still has a certain expansion ratio for the valve of the patient. However, because the physiological structure and the pathological mechanism of the atrioventricular valve (including the mitral valve and the tricuspid valve) are complicated, it is quite difficult to accurately position and fix the products. Currently, for the technique of atrioventricular valve intervention and replacement, corporations like Edwards Corporation, Medtronic Corporation and Tiara Corporation, without exception, are required to provide a certain radial expansion ratio to satisfy the demand of anchoring. Although they employ valve leaflet clamping to improve anchoring effect, the radial expansion ratio is just slightly reduced. In general, the conventional anchoring techniques mostly rely on the supporting force exerted on the atrioventricular valve annulus by the supporting frame. Doctors usually select a valve specification larger than the autogenous atrioventricular valve annulus of the patient to conform to the contour of the mitral valve tissue. The huge supporting frame itself not only affects the outflow tract, but also easily presses the surrounding tissues, and further blocks the blood flow in the left ventricular outflow tract. As for the mitral valve replacement, the supporting frame specification is so large that the anterior valve of the mitral valve is easily pushed toward the left ventricular outflow tract. The valve leaflet clamping, which is provided and introduced to fix the anterior valve of the mitral valve, makes the releasing steps extremely complicated and be influenced by the calcification degree of the valve leaflet, which affects the success rate of the operation. Furthermore, in the prior art the supporting frame portion located in the atrium mostly employs the lattice form, the huge supporting force of which easily presses the heart tissue, and which cannot completely conform to the non-uniform contour of the atrial wall or of the native valve annulus of the patient. Those defects are frequently reported in the clinical reports of the above technologies.

Figure 1B:
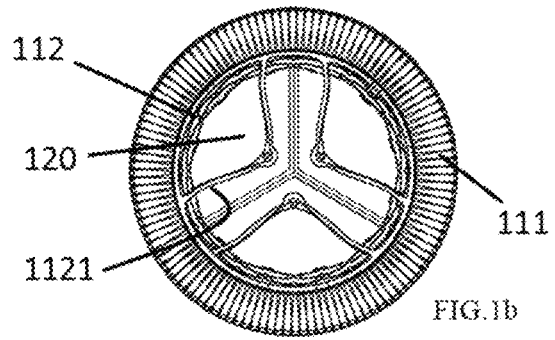
Figure 1C:
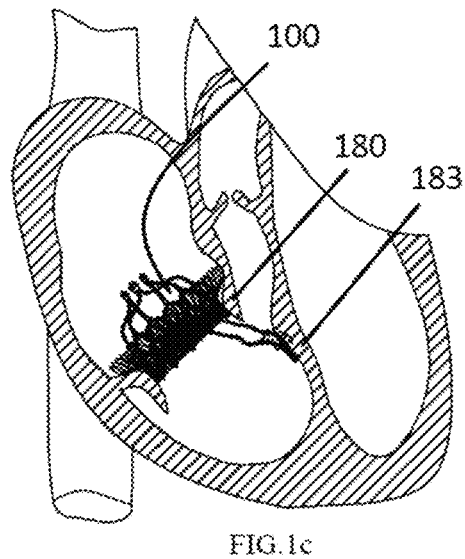

Therefore, the present application provides a novel heart valve prosthesis that can solve the above problems. In an embodiment, as shown in FIGS. 1a-1c, a heart valve prosthesis 100 anchored to an interventricular septum is provided for tricuspid valve intervention and replacement treatment, wherein the heart valve prosthesis comprises a valve supporting frame 110 and a fixing device 113; the valve supporting frame 110 comprises a valve stitching section 112 and an artificial valve 120; the valve stitching section 112 is a tube-like lattice structure; the artificial valve 120 is fixedly connected to the valve stitching section 112; the fixing device 113 comprises a fixing and supporting section 114 and a fixing member 115; one end of the fixing and supporting section 114 is connected to a proximal end portion of the valve stitching section 112, and the other end of the fixing and supporting section 114 is connected to the interventricular septum 183 of the patient by the fixing member 115, to support the heart valve prosthesis 100 and limit the axial movement of the heart valve prosthesis 100. The heart valve prosthesis 100 further comprises a ring 111; the ring 111 is connected to the valve stitching section 112, and in a free state, the ring 111 is located in the atrium of the patient and clings to the native valve annulus 180 of the patient. In the design of most of the products in the prior art, the valve annulus is supported by a supporting frame; what different from the prior art are that, in the present application, the fixing and supporting section 114 is fixed to the interventricular septum 183 of the patient by the fixing member 115, and such an anchoring mode enables the valve supporting frame 110 to obtain a anchoring force large enough, without radially dilating the native valve annulus of the patient. The fixing and supporting section 114 is an extension of the proximal skeleton of the valve stitching section 112, and the fixing and supporting section 114 is rigid. In such a design, it is considered that the whole apparatus is supported in the target position by the fixing device 113, and the rigidity design may ensure the anchoring function. The distal skeleton of the valve stitching section 112 is provided with an extension section 1121, which enables the supporting frame to be controllably released, to improve the positioning accuracy.

Figure 2E:
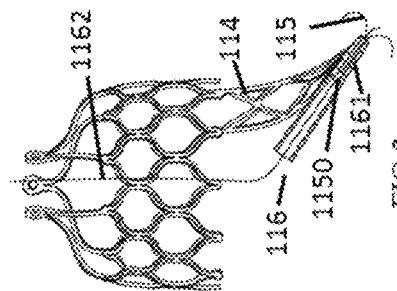
FIGS. 2a-2f are schematic diagrams illustrating multiple embodiments of the present application.
Figure 2F:
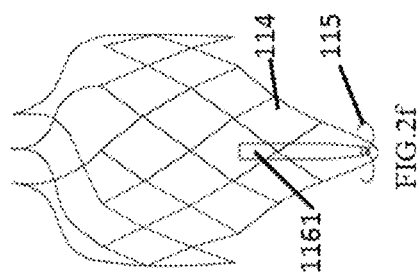
Figure 2C:
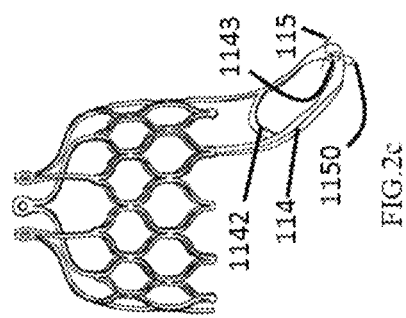
Figure 2D:
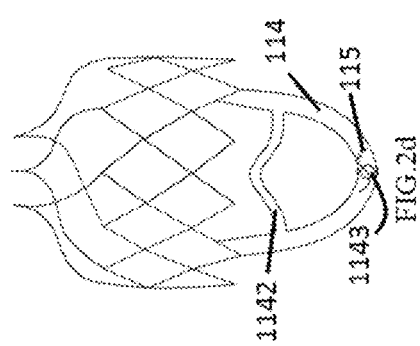
Figure 2A:
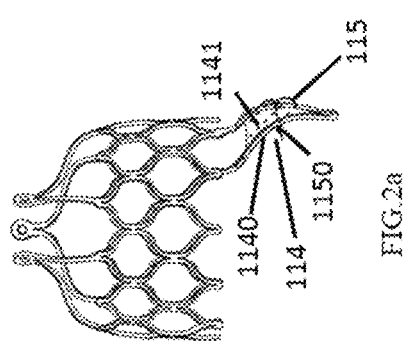
Figure 2B:
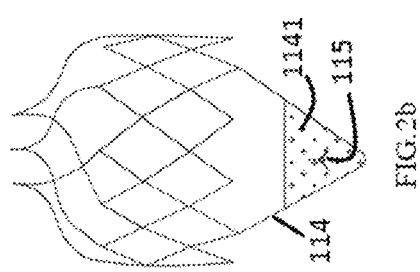
Figure 2G:
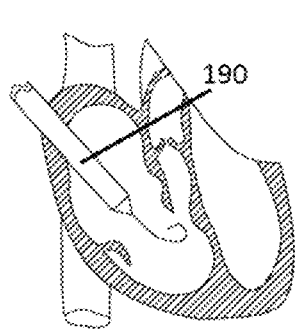
FIGS. 2g-2j are schematic diagrams illustrating a conveying mode of the present application.
Figure 2H:
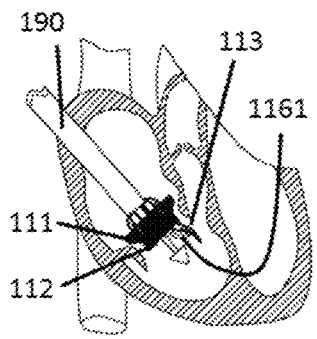
Figure 2K:
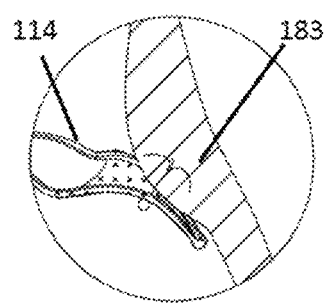
FIG. 2k is a partial enlarged view of FIG. 2j.
Figure 2I:
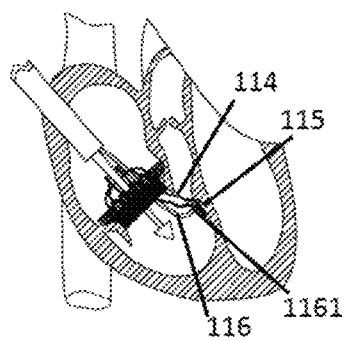
Figure 2J:
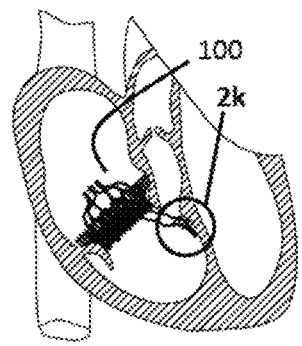

In an embodiment, as shown in FIGS. 2a and 2b, the fixing and supporting section 114 is formed by a plurality of rods. One end of each of the plurality of rods is connected to the valve stitching section 112, and the other ends of the plurality of rods are mutually connected and are connected to the interventricular septum of the patient by the fixing member 115. The fixing and supporting section 114 is a triangular structure, the fixing and supporting section 114 is provided with a curved section 1140, thereby enabling the proximal end portion of the fixing and supporting section 114 to cling to the interventricular septum of the patient. The contact part of the fixing and supporting section 114 and the interventricular septum 183 of the patient is a straight line section (as shown in FIG. 2k). Such a design can increase the contact area between the fixing and supporting section 114 and the interventricular septum 183 of the patient to the utmost extent, thereby enhancing the anchoring effect. The fixing member 115 is an anchoring needle, and the distal portion of the anchoring needle 115 is pre-shaped. The needle point portion of the anchoring needle 115 is pre-shaped to be spiral, circular or arcuate, and the needle point portion of the anchoring needle 115 has a plurality of barbs. The tail portion of the anchoring needle 115 is provided with a stopper 1150, and the diameter of the stopper 1150 is greater than the needle diameter of the anchoring needle 115. The fixing and supporting section 114 is covered with a film 1141, and the material of the film 1141 comprises metal material, polytetrafluoroethylene, polyethylene, polypropylene, terylene or animal-derived material. The needle point portion of the anchoring needle 115 passes through the film 1141 and is inserted into the heart tissue of the patient.

In another embodiment, as shown in FIGS. 2c and 2d, the fixing and supporting section 114 is an arcuate structure, and the fixing and supporting section 114 is provided therein with an enhancing rod 1142. The advantage of such a design is that the rigidity of the fixing and supporting section 114 is improved, thereby ensuring the anchoring function. The fixing member 115 is an anchoring needle, and the distal portion of the anchoring needle 115 is pre-shaped. The needle point portion of the anchoring needle 115 is pre-shaped to be a combination of arc line and straight line, or to be branched double hooks, and the needle point portion of the anchoring needle 115 has one barb. The tail portion of the anchoring needle 115 is provided with a stopper 1150. The fixing and supporting section 114 is provided with an opening 1143, and the needle point portion of the anchoring needle 115 passes through the opening 1143 and is inserted into the heart tissue of the patient. The diameter of the stopper 1150 is greater than the aperture of the opening 1143.

In another embodiment, as shown in FIGS. 2e-2f, the fixing and supporting section 114 is a net-like structure. The fixing member 115 is an anchoring needle, the distal portion of the anchoring needle 115 is pre-shaped, and the needle point portion of the anchoring needle 115 is pre-shaped to be a three-dimensional bent shape or a multi-sectioned bent shape. The needle point portion of the anchoring needle 115 is not provided with any barbs, and the tail portion of the anchoring needle 115 is provided with a stopper 1150. The fixing device 113 comprises a fixing member pushing system 116, and the fixing member pushing system 116 pushes the fixing member 115, so that one end of the fixing and supporting section 114 is fixed on the interventricular septum of the patient. The fixing member pushing system 116 comprises a guide rail 1161 and a mandril 1162; the guide rail 1161 is fixedly provided on the fixing and supporting section 114; the ends of the guide rail 1161 have a necking; the anchoring needle 115 and the mandril 1162 are provided within the guide rail 1161; by operating the mandril 1162, the needle point portion of the anchoring needle 115 passes through the guide rail 1161 and is inserted into the interventricular septum of the patient; and the diameter of the stopper 1150 is greater than the aperture of the necking. After it is confirmed that the anchoring effect of the anchoring needle 115 is ideal, the mandril 1162 is withdrawn from the human body.

In an embodiment, as shown in FIGS. 2g-2k, a conveying conduit 190 loaded with the heart valve prosthesis 100 is introduced via a minimally invasive incision in the right atrial wall to the tricuspid valve annulus. Operate the conveying conduit 190 gradually, so that the fixing device 113 can be firstly released; and continue operating the conveying conduit 190, so that the valve stitching section 112 is partially released, till the ring 111 is released. At this point, the valve stitching section 112 has not been completely detached from the conveying conduit 190, so the process is reversible. The ring 111 is positioned by the tricuspid valve annulus, and completely releases the valve stitching section 112 after being positioned. The fixing device 113 comprises a fixing member pushing system 116, and the fixing member pushing system 116 comprises a guide rail 1161 and a mandril (not labeled). The ends of the guide rail 1161 have a necking, and the anchoring needle 115 and the mandril are provided within the guide rail 1161. Through operating the mandril, the needle point portion of the anchoring needle 115 passes through the guide rail 1161 and is inserted into the interventricular septum of the patient. The diameter of the stopper 1150 is greater than the aperture of the necking. The guide rail 1161 is connected to the fixing and supporting section 114 by a detachable connection (the connection mode may adopt well-known techniques, such as rope and slipknot), and after it is confirmed that the anchoring effect of the anchoring needle 115 is ideal, by removing the detachable connection, the fixing-member pushing system 116 (comprising the guide rail 1161 and the mandril) and the conveying conduit 190 may be withdrawn from the human body. The advantage of such a design is that the volume of the implant can be reduced, thereby lowering the risk of thrombosis.

Figure 2L:
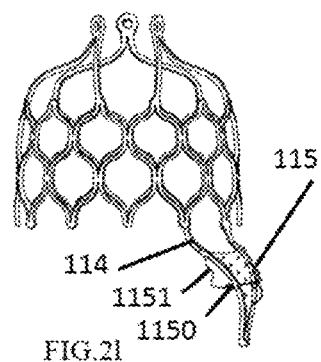
FIG. 2l is a schematic diagram illustrating another embodiment of the present application.

In another embodiment, as shown in FIG. 2l, the stopper 1150 is provided with a connector 1151, and the connector 1151 is a wire-shaped member. One end of the connector 1151 is connected to the fixing and supporting section 114, and the other end of the connector 1151 is connected to the stopper 1150. Such a design mainly can ensure that the implanting instrument is detachably connected with the pushing system, thereby improving the accuracy of the needle inserting, and preventing the anchoring needle from deviating from the predetermined needle inserting point.

Embodiment 2

Figure 3A:
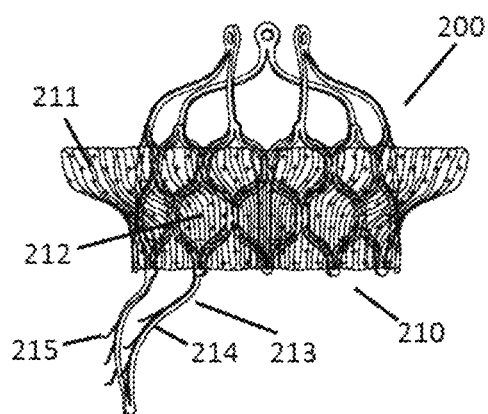
FIGS. 3a-3e are schematic diagrams illustrating multiple embodiments of the present application.
Figure 3B:
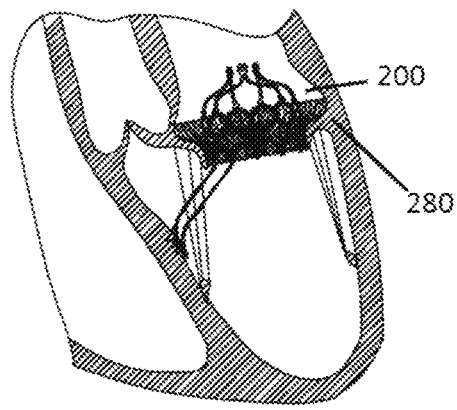

In an embodiment, as shown in FIGS. 3a and 3b, a heart valve prosthesis 200 anchored to an interventricular septum is provided for mitral valve intervention and replacement treatment. The heart valve prosthesis comprises a valve supporting frame 210 and a fixing device 213; the valve supporting frame 210 comprises a valve stitching section 212 and an artificial valve (not shown); the artificial valve is fixedly connected to the valve stitching section 212; the fixing device 213 comprises a fixing and supporting section 214 and a fixing member 215; one end of the fixing and supporting section 214 is connected to a proximal portion of the valve stitching section 212, and the other end of the fixing and supporting section 214 is connected to the interventricular septum of the patient by the fixing member 215, to support the heart valve prosthesis 200 and limit the axial movement of the heart valve prosthesis 200. The heart valve prosthesis 200 further comprises a ring 211, and the ring 211 is connected to the valve stitching section 212. In a free state, the ring 211 is located in the atrium of the patient and clings to the native valve annulus 280 of the patient.

Figure 3C:
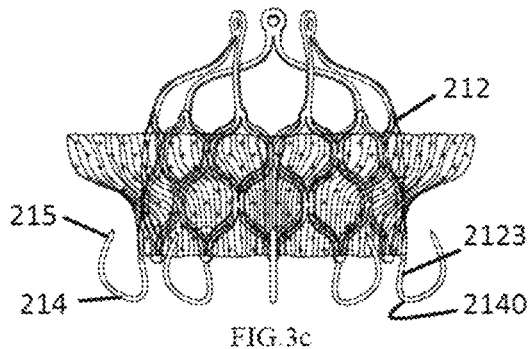

In an embodiment, as shown in FIG. 3c, the fixing and supporting section 214 includes a plurality of rods 2123, and one end of each of the plurality of rods 2123 is formed by the extended partial rods in the proximal skeleton of the valve stitching section 212. For example, the plurality of rods 2123 are the extended wave peaks of the zigzag-form wave in the lattice structure of the valve stitching section 212, and the other end of each of the plurality of rods 2123 is connected to the interventricular septum of the patient by the fixing member 215. The fixing and supporting section 214 and the fixing member 215 are an integral structure, and the fixing member 215 is a sharp structure at the ends of the rods 2123. The rods 2123 are provided with a curved section 2140, so that the sharp structure of the rods 2123 can be inserted into the interventricular septum of the patient.

Figure 3D:
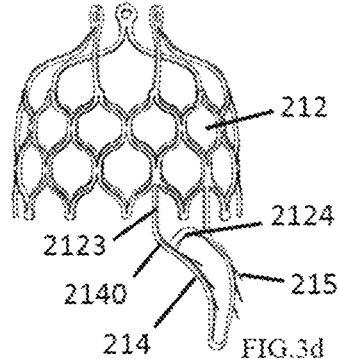
Figure 3E:
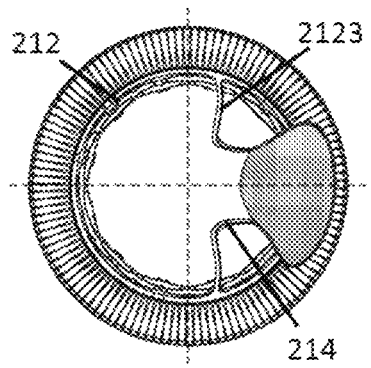

In another embodiment, as shown in FIG. 3d, the fixing and supporting section 214 is formed by partial rods 2123 of the proximal skeleton of the valve stitching section 212; the rods 2123 are disposed between the neighboring zigzag-form waves or between the neighboring wave-shaped structures in the lattice structure of the valve stitching section 212, and the rods 2123 are provided with a strengthening wave 2124 therebetween, to intensify the transverse supporting force between the rods 2123. The fixing and supporting section 214 and the fixing member 215 are an integral structure, and the fixing member 215 is one or more barbs. The fixing and supporting section 214 is provided with a curved section 2140, to enable the proximal portion of the fixing device 213 to cling to the interventricular septum of the patient, so that the barb can be inserted into the interventricular septum of the patient. As shown in FIG. 3e, on the circumferential circular arc where the outer edge of the valve stitching section 212 is located, the largest arc length that is formed by the connection points of the plurality of rods 2123 and the valve stitching section 212 is greater than or equal to a quarter of the perimeter of the valve stitching section 212. The advantage of such a design is that the fulcrum of the fixing and supporting section 214, which is disposed on the valve stitching section 212, can provide sufficient supporting strength and rigidity, thereby avoiding incline of the valve stitching section 212.

Figure 4A:
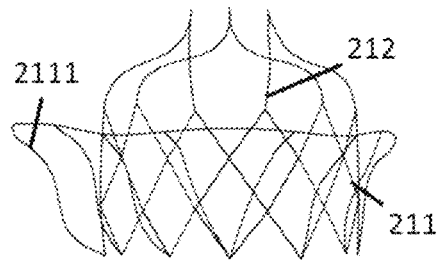
Figure 4B:
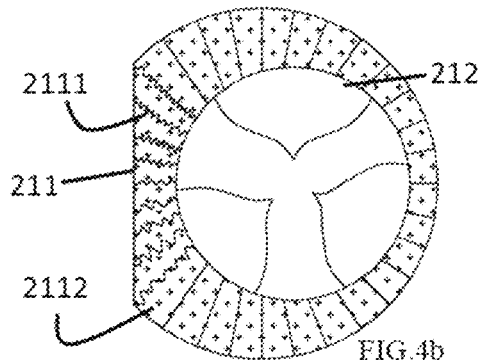

In an embodiment, as shown in FIGS. 4a and 4b, the ring 211 and the valve stitching section 212 are an integral structure; the ring 211 has a skeleton 2111 made of a shape memory alloy; the skeleton 2111 is entirely covered with a film 2112; the skeleton 2111 includes a plurality of supporting rods; the supporting rods are formed by partial rods of the valve stitching section 212, and the width of the supporting rod is 0.4 mm. In a cross-section perpendicular to the central axis of the artificial valve, the projection of the ring 211 is a D-shaped ring structure, and the valve stitching section 212 is disposed in the ring 211. More preferably, the supporting rod 2111 is a wave-shaped structure. The advantage of such a design is that the flexibility of the skeleton 2111 is improved, so that the ring 211 may conform to the non-uniform contour of the atrial wall or of the native valve annulus of the patient, thereby improving the leak resistance effect.

Figure 4C:
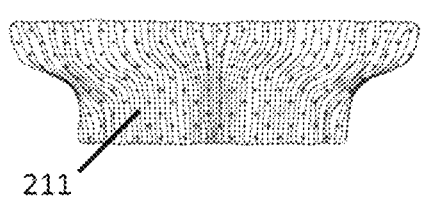

In the product in the prior art, the supporting frame disposed in the atrium mostly employs the lattice form, and the huge supporting force of the supporting frame easily presses the heart tissue, and the leak resistance effect is unsatisfying. What different from the supporting frame in the prior art are that, the ring 211 of the present application is disposed in the atrium of the patient and clings to the native valve annulus of the patient, and the ring 211 may conform to the non-uniform contour of the atrial wall or of the native valve annulus of the patient, thereby improving the leak resistance effect. In an embodiment, as shown in FIG. 4c, in a longitudinal section parallel to a central axis of the artificial valve, the projection of the ring 211 is a disk-like structure. As shown in FIGS. 4d-4f, the ring 211 has a skeleton 2111 made of a shape memory alloy; the skeleton 2111 is entirely covered with a film 2112; and the material of the film 2112 comprises metal material, polytetrafluoroethylene, polyethylene, polypropylene, terylene or animal-derived material. The skeleton 2111 is a wave-shaped structure, a saw-shaped structure or a lattice structure that is formed by winding a metal memory material wire. The diameter of the metal memory material wire (for example, a nickel titanium alloy wire) is 0.3 mm. The ring 211 and the valve stitching section 212 are made separately and independently and then connected to form an integral structure by stitching with a suture.

Embodiment 3

In an embodiment, as shown in FIGS. 5a-5c, a heart valve prosthesis 300 anchored to an interventricular septum is provided for tricuspid valve intervention and replacement treatment, wherein the heart valve prosthesis comprises a valve supporting frame 310 and a fixing device 313; the valve supporting frame 310 comprises a valve stitching section 312 and an artificial valve (not shown); the artificial valve is fixedly connected to the valve stitching section 312; the valve stitching section 312 is a tube-like wave-shaped structure; the fixing device 313 comprises a fixing and supporting section 314 and a fixing member 315; the fixing and supporting section 314 is an inverted cone-shaped structure; the fixing and supporting section 314 includes a plurality of rods or wires; one end of the fixing and supporting section 314, which has a larger diameter, is connected to the proximal end of the valve stitching section 312 through well-known techniques such as stitching, clipping or welding; one end of the fixing and supporting section 314, which has a smaller diameter, is provided with a connecting rod 317; the connecting rod 317 is rigid; one end of the connecting rod 317 is connected to one end of the fixing and supporting section 314; the proximal portion of the connecting rod 317 is provided with the fixing member 315, and in a free state, the fixing member 315 is fixed on the interventricular septum 383 of the patient, to support the heart valve prosthesis 300 and limit the axial movement of the heart valve prosthesis 300. The heart valve prosthesis 300 further comprises a ring 311, and the ring 311 is connected to the valve stitching section 312.

The proximal portion of the connecting rod 317 is a hollow tube, and the tube wall is provided with an opening 3170. The furthest distal end of the fixing member 315 is sharp, and the distal portion of the fixing member 315 is pre-shaped. The distal end portion of the fixing member 315 is pre-shaped to be one of or a combination of the following shapes: spiral, circle, arc, a combination of arc and straight line, branched double hooks, three-dimensional bent shape, and multi-section bent shape. The distal end of the fixing member 315 does not have a barb, or has one or more barbs. In a free state, the furthest distal end of the fixing member 315 protrudes out of the opening 3170 in the hollow tube 317 and is inserted into the interventricular septum 383.

The ring 311 is connected to the valve stitching section 312, and in a free state, the ring 311 is disposed in the atrium of the patient and clings to the native valve annulus 380 of the patient. The cross-sectional area of the ring 311 is greater than the cross-sectional area of the native valve annulus 380 (the dotted lines shown in FIGS. 5b and 5c) of the patient, and the ring 311 may conform to the non-uniform contour of the atrial wall or of the native valve annulus of the patient and does not restrict the contraction function of the atrium. In a cross-section perpendicular to the central axis of the artificial valve, the projection of the ring 311 is a ring-shaped structure, and the ring-shaped structure comprises a circular structure (FIG. 5b) or an elliptic structure (FIG. 5c).

Figure 5D:
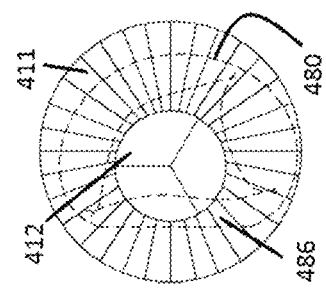

In an embodiment, as shown in FIG. 5d, in a longitudinal section parallel to a central axis of the artificial valve, the projection of the ring 311 is a bowl-like structure, and the bowl opening is supported within the atrium 381 of the patient. The ring 311 has a skeleton 3111 made of a shape memory alloy, and the skeleton 3111 is partially covered with a film 3112, so as to prevent the ring 311 supported within the atrial wall from blocking the coronary sinus, the superior vena cava and the inferior vena cava. The material of the film 3112 comprises metal material, polytetrafluoroethylene, polyethylene, polypropylene, terylene or animal-derived material.

Embodiment 4

Figure 6C:
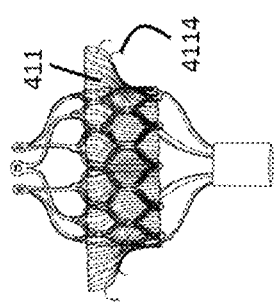
FIGS. 6a-6e are schematic diagrams illustrating multiple embodiments of the present application.
Figure 6B:
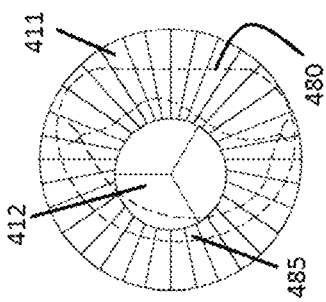
Figure 6D:
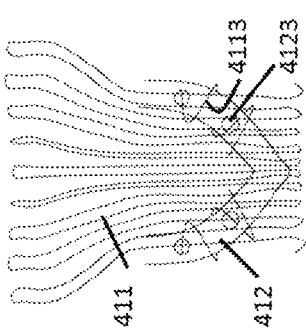
Figure 6A:
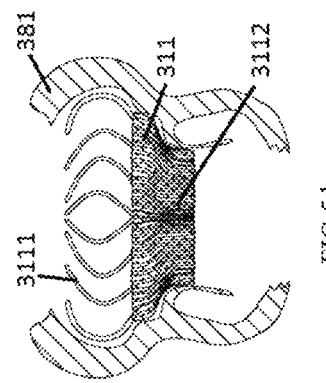

In an embodiment, as shown in FIG. 6a, a heart valve prosthesis 400 anchored to an interventricular septum is provided for tricuspid valve intervention and replacement treatment. This embodiment is different from embodiment 3 in that, the fixing member 415 is a supporting frame having two larger end portions and a smaller middle portion, and is formed by a shape memory alloy, and in a free state, the fixing member 415 is fixed to the interventricular septum 483.

In an embodiment, what different from the concentric structure of most of the conventional products are that: in the present application, in a cross-section perpendicular to the central axis of the artificial valve, the projection of the ring 411 is a circular ring-shaped structure; the valve stitching section 412 is disposed in the ring 411; and the cross-sectional area of the valve stitching section 412 is less than the cross-sectional area of the native valve annulus 480 of the patient, which prevents the valve stitching section 412 radially dilating the native valve annulus 480 of the patient. Such a design not only reduces the influence on the outflow tract after the supporting frame is released, and avoids the traction to the protogenetic valve annulus, but also ensures that the opening area of the valve will not change greatly because of the huge difference between the valve annulus of patients, thereby optimizing the performance of the valve, and moreover, the manufacturers may reduce the product specifications, which alleviates the goods stocking pressure of the manufacturers. The center of the valve stitching section 412 and the center of the ring 411 are not coincident, and the ring 411 is eccentrically arranged relative to the valve stitching section 412. As shown in FIG. 6b, when the heart valve prosthesis 400 is used for mitral valve intervention and replacement, the central axis of the valve stitching section 412 deviates toward the posterior valve region 485 (shown by dotted lines) of the mitral valve of the patient, which can further reduce the block to the left ventricular outflow tract. As shown in FIG. 6c, when the heart valve prosthesis 400 is used for tricuspid valve intervention and replacement, the central axis of the valve stitching section 412 deviates toward the cuspis medialis region 486 (shown by dotted lines) of the tricuspid valve of the patient, which facilitates the fixing device clinging to the target anchoring region, thereby obtaining a more ideal anchoring effect, and more stable movement of the valve.

Figure 6E:
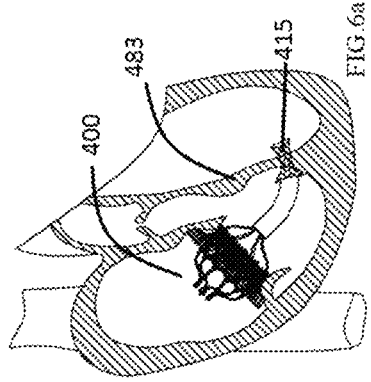

In an embodiment, as shown in FIGS. 6d and 6e, the ring 411 and the valve stitching section 412 are made separately and independently and then connected to form an integral structure. The skeleton of the valve stitching section 412 is provided with an opening 4123, and the ring 411 passes through the opening 4123 and is connected to the valve stitching section 412 with a suture 4113. The ring 411 has a skeleton made of a shape memory alloy, and the skeleton is entirely covered with a film. In a longitudinal section parallel to a central axis of the artificial valve, the projection of the ring 411 is a disk-like structure. The ring 411 is provided with a barb 4114, and when the ring 411 clings to the native valve annulus of the patient, the barb 4114 is inserted into the autologous tissue of the patient.

Embodiment 5

Figure 7A:
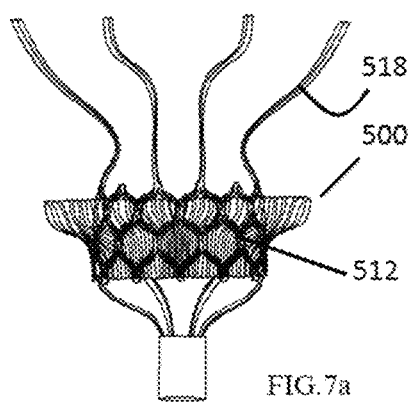
FIGS. 7a-7d are schematic diagrams illustrating multiple embodiments of the present application.
Figure 7C:
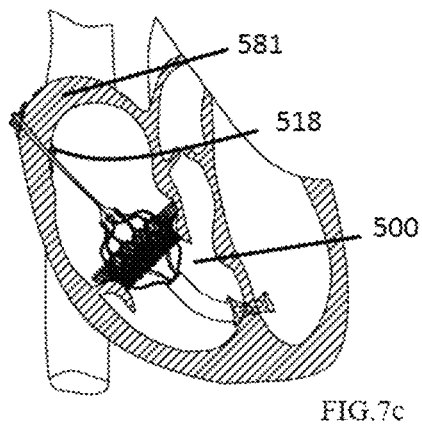
Figure 7B:
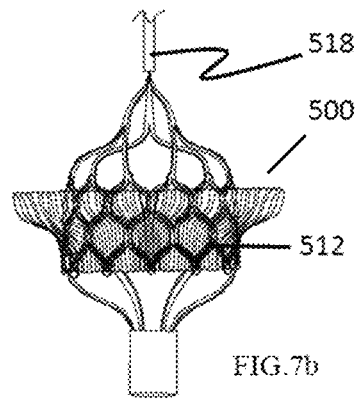

In an embodiment, as shown in FIGS. 7a and 7b, what different from the above embodiments are that, the heart valve prosthesis 500 further comprises an auxiliary fixing device 518; the auxiliary fixing device 518 is a wire or a rod; one end of the auxiliary fixing device 518 is connected to the valve stitching section 512, and the other end of the auxiliary fixing device 518 is fixed on an atrium tissue of the patient. The advantage of such a design is that displacement or disengagement of the implant can be avoided by means of upper and lower location limiting, thereby enhancing the anchoring fastness of the implant.

Figure 7D:
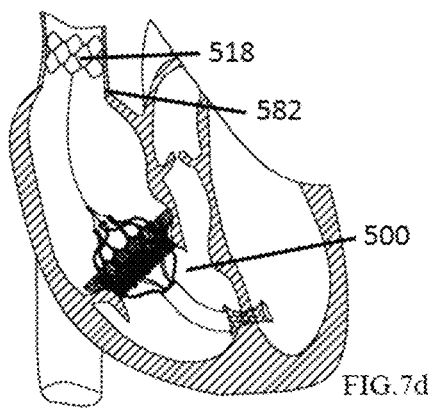

In another embodiment, as shown in FIG. 7c, the auxiliary fixing device 518 is a supporting frame having two larger end portions and a smaller middle portion, and is formed by a shape memory alloy. In a free state, the auxiliary fixing device 518 is fixed on the atrial wall 581. In another embodiment, as shown in FIG. 7d, the auxiliary fixing device 518 is a tube-like supporting frame, and in a free state, the auxiliary fixing device 518 is fixed in the superior vena cava 582.

Figure 8A:
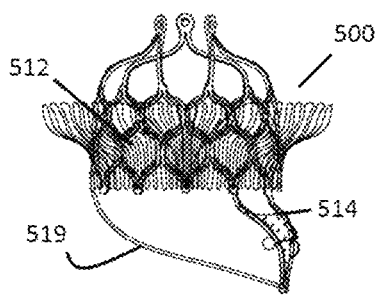
FIGS. 8a-8d are schematic diagrams illustrating multiple embodiments of the present application.
Figure 8C:
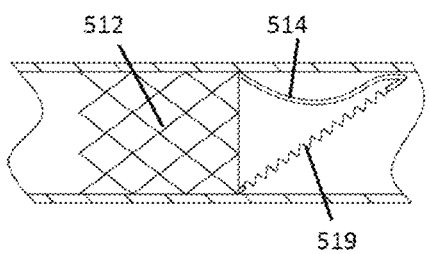
Figure 8B:
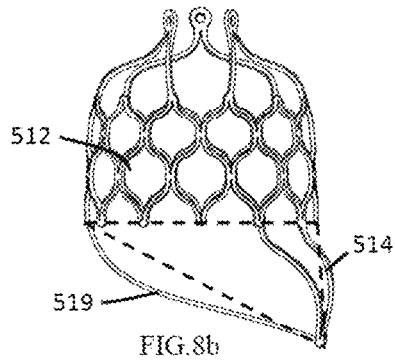
Figure 8D:
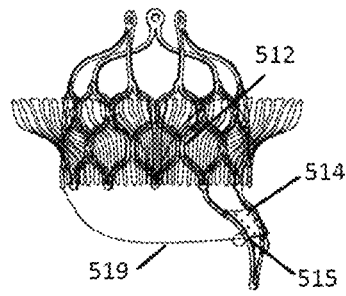

In an embodiment, as shown in FIG. 8a, the heart valve prosthesis 500 further comprises an auxiliary stabilizing device 519. The proximal end of the auxiliary stabilizing device 519 is connected to the fixing and supporting section 514, and the distal end of the auxiliary stabilizing device 519 is connected to the valve stitching section 512. In a longitudinal section parallel to a central axis of the artificial valve, the projections of the valve stitching section 512, of the fixing and supporting section 514 and of the auxiliary stabilizing device 519 are connected to become a closed structure, which enables the implant to be more secure in the target position while ensuring the operation convenience of fixing on one side, thereby preventing the implant from losing balance in the body of the patient. As shown in FIG. 8b, in order to maximize the above balancing effect, the distal end of the auxiliary stabilizing device 519 is connected to the position with the maximum diameter of the valve stitching section 512. In a longitudinal section parallel to a central axis of the artificial valve, the projections of the valve stitching section 512, of the fixing and supporting section 514 and of the auxiliary stabilizing device 519 are connected to become a triangle. In consideration of the uniformity of the length of the compressed fixing and supporting section 514 and the length of the compressed the auxiliary stabilizing device 519, as shown in FIG. 8c, the auxiliary stabilizing device 519 is designed to be a wire or a wave-like rod. In another embodiment, as shown in FIG. 8d, the proximal end of the auxiliary stabilizing device 519 is connected to the fixing member 515, and the distal end of the auxiliary stabilizing device 519 is connected to the valve stitching section 512.

Figure 9A:
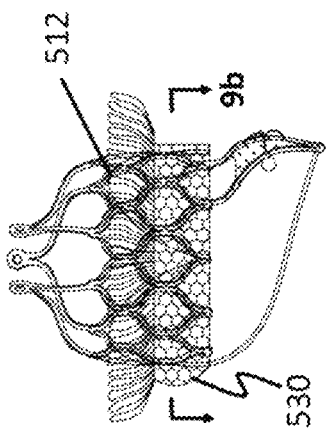
Figure 9C:
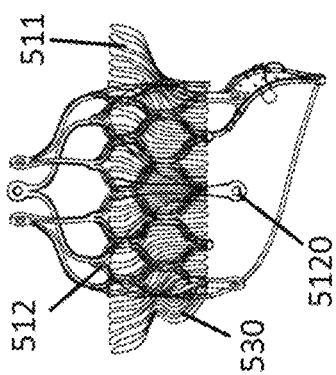

In another embodiment, as shown in FIG. 9a, an outer surface of the valve stitching section 512 is further provided with a filling device 530. In a cross-section perpendicular to the central axis of the artificial valve 520, as shown in FIG. 9b, the projection of the filling device 530 is a ring-shaped structure, and the ring-shaped structure comprises a circular ring structure or a D-shaped ring structure. The advantage of such a design is that the contact with the native valve is increased, thereby improving the leak resistance effect. The filling device 530 has a skeleton made of a shape memory alloy, the skeleton is partially or entirely covered with a film, and the film material comprises metal material, polytetrafluoroethylene, polyethylene, polypropylene, terylene or animal-derived material. In another embodiment, as shown in FIG. 9c, the filling device 530 and the ring 511 are an integral structure. The proximal skeleton 5120 of the valve stitching section 512 is partially extended. Such a design enables the ring 511 to expand firstly while the proximal end of the valve stitching section 512 remains compressed, which facilitates adjusting the position of the supporting frame, thereby preventing the proximal end of the supporting frame from stabbing the blood vessel wall due to expanding in the adjusting process.

Figure 9E:
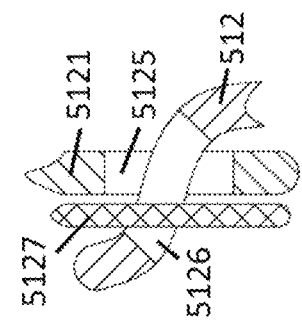
Figure 9B:
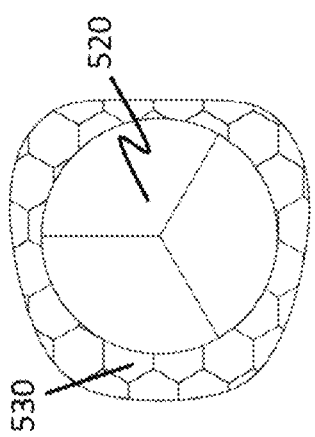
Figure 9D:
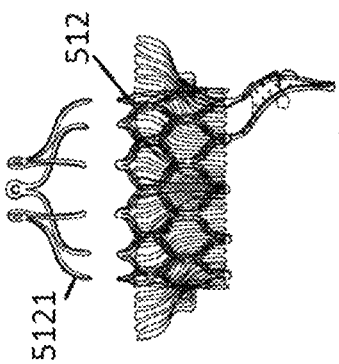
Figure 9F:
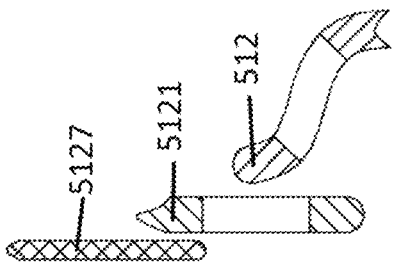

In another embodiment, as shown in FIGS. 9d-9f, the distal skeleton of the valve stitching section 512 is provided with an extended section 5121, and the extended section 5121 and the valve stitching section 512 are detachably connected. Such a design ensures that the extended section 5121 may be withdrawn from the human body while the supporting frame is ensured to be controllably released, thereby greatly reducing the implant, reducing the contact and stimulation to the atrium, facilitating the conveying system being removed from the human body, and eliminating the limitation to the valve-in-valve implantation in future. As shown in FIG. 9e, the proximal end of the extended section 5121 is provided with a hole-like structure 5125; the distal skeleton of the valve stitching section 512 enters the hole-like structure 5125 in a staggered way; the distal skeleton of the valve stitching section 512 is provided with a locking hole 5126, and the locking is realized by inserting a locking rod 5127 into the locking hole 5126. As shown in FIG. 9f, when the locking rod 5127 is pulled out of the locking hole 5126, the distal skeleton of the valve stitching section 512 is separated from the hole-like structure 5125 of the extended section 5121, to realize the detaching of the extension section 5121 and the valve stitching section 512.

Finally, it should be understood that, the above descriptions are merely preferable embodiments of the present application, and are not intended to limit the present application. Any modifications, equivalent substitutions and improvements that are made within the spirits and principles of the present application are all within the protection scope of the present application.

What is claimed is:

1. A heart valve prosthesis anchored to an interventricular septum, comprising a valve supporting frame and a fixing device; the valve supporting frame comprises a valve stitching section and an artificial valve; the artificial valve is fixedly connected to the valve stitching section; the fixing device comprises only one fixing and supporting section and a fixing member, and the fixing and supporting section and the fixing member are two different components; one end of the fixing and supporting section is connected to a proximal portion of the valve stitching section; and another end of the fixing and supporting section is connected only to the interventricular septum of a patient by the fixing member, to support the heart valve prosthesis and limit axial movement of the heart valve prosthesis;
wherein the heart valve prosthesis further comprises a ring; the ring is connected to a main body of the valve stitching section, at a distal end of the valve stitching section, an end face of the ring is not higher than the valve stitching section; and in a free state, part of the ring is placed in the patient's atrium;
wherein in a cross-section perpendicular to a central axis of the artificial valve, a center of the valve stitching section and a center of the ring are not coincident.

2. The heart valve prosthesis anchored to the interventricular septum according to claim 1, wherein the fixing device comprises a fixing member pushing system; and the fixing member pushing system is configured to push the fixing member so that one end of the fixing and supporting section is fixed on the interventricular septum of the patient.

3. The heart valve prosthesis anchored to the interventricular septum according to claim 1, the fixing and supporting section is covered with a film.

4. The heart valve prosthesis anchored to the interventricular septum according to claim 1, wherein the heart valve prosthesis further comprises an auxiliary fixing device; one end of the auxiliary fixing device is connected to a distal end of the valve stitching section, and another end of the auxiliary fixing device is anchored on an atrium tissue.

5. The heart valve prosthesis anchored to the interventricular septum according to claim 1, wherein the heart valve prosthesis further comprises an auxiliary fixing device; one end of the auxiliary fixing device is connected to a distal end of the valve stitching section, and another end of the auxiliary fixing device is anchored in a blood vessel of the patient.

6. The heart valve prosthesis anchored to the interventricular septum according to claim 1, wherein the heart valve prosthesis further comprises an auxiliary stabilizing device; a proximal end of the auxiliary stabilizing device is connected to the fixing and supporting section; and a distal end of the auxiliary stabilizing device is connected to the valve stitching section.

7. The heart valve prosthesis anchored to the interventricular septum according to claim 1, wherein the heart valve prosthesis further comprises an auxiliary stabilizing device; a proximal end of the auxiliary stabilizing device is connected to the fixing member; and a distal end of the auxiliary stabilizing device is connected to the valve stitching section.

8. The heart valve prosthesis anchored to the interventricular septum according to claim 6, wherein the auxiliary stabilizing device is one of a wire and a rod.

9. The heart valve prosthesis anchored to the interventricular septum according to claim 7, wherein the auxiliary stabilizing device is one of a wire and a rod.

10. The heart valve prosthesis anchored to the interventricular septum according to claim 1, wherein a filling device is arranged on an outer surface of the valve stitching section.

* * * * *